United States Patent
Vanderbilt et al.

(10) Patent No.: US 7,780,678 B2
(45) Date of Patent: Aug. 24, 2010

(54) THERMAL TREATMENT TO IMPROVE INTRAOCULAR LENS INSERTER LUBRICITY

(75) Inventors: David P. Vanderbilt, Webster, NY (US); Li-Chun Tsou, Rochester, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 1882 days.

(21) Appl. No.: 10/640,131

(22) Filed: Aug. 13, 2003

(65) Prior Publication Data
US 2005/0038446 A1    Feb. 17, 2005

(51) Int. Cl.
*A61F 9/00*   (2006.01)
(52) U.S. Cl. .................................... 606/107
(58) Field of Classification Search .................. 606/107
See application file for complete search history.

(56) References Cited

U.S. PATENT DOCUMENTS

| 4,681,102 A | 7/1987 | Bartell ..................... 128/303 |
| 5,186,972 A | 2/1993 | Williams et al. |
| 5,275,604 A | 1/1994 | Rheinish et al. ............. 606/107 |
| 5,304,182 A | 4/1994 | Rheinish et al. ............. 606/107 |
| 5,716,364 A * | 2/1998 | Makker et al. .............. 606/107 |
| 5,756,144 A | 5/1998 | Wolff et al. |
| 5,944,725 A | 8/1999 | Cicenas et al. ............. 606/107 |
| 6,371,960 B2 | 4/2002 | Heyman et al. ............. 606/107 |

FOREIGN PATENT DOCUMENTS

| EP | 1369136 A1 | 12/2003 |
| WO | WO 01/10352 A1 | 2/2001 |

* cited by examiner

*Primary Examiner*—Todd E Manahan
*Assistant Examiner*—Katherine M Dowe
(74) *Attorney, Agent, or Firm*—Joseph Barrera

(57) ABSTRACT

Methods for enhancing the lubricity of implant delivery devices are provided. The present methods of enhancing the lubricity of an intraocular lens inserter reduce the force required to express an intraocular lens therefrom. By reducing the force required to express an intraocular lens from an inserter, intraocular lens delivery is improved.

22 Claims, No Drawings

THERMAL TREATMENT TO IMPROVE INTRAOCULAR LENS INSERTER LUBRICITY

FIELD OF THE INVENTION

The present invention relates to methods for enhancing the lubricity of implant delivery devices. More specifically, the subject invention relates to methods of enhancing the lubricity of an intraocular lens inserter to reduce the force required to express an intraocular lens therefrom.

BACKGROUND OF THE INVENTION

The natural crystalline lens of the eye plays a primary role in focusing light onto the retina for proper vision. However, vision through the natural lens may become impaired due to an injury, or due to the formation of a cataract caused by aging or disease. To restore vision, the natural lens is typically replaced with an artificial lens. An artificial lens may also be implanted to make a refractive correction.

Many surgical procedures have been developed for removing the natural lens. Typically, a slender implement is inserted through a small incision in the eye to contact the natural lens. The implement includes a cutting tip that is ultrasonically vibrated to emulsify the lens. The emulsified fragments of the lens are then aspirated out of the eye through a passage provided in the cutting tip. The slender nature of the implement enables extraction of the lens through a small incision in the eye. The use of a small incision over other procedures requiring a large incision can lessen the trauma and complications experienced during the surgery and postoperatively.

Because the incision required to remove the lens is small, the development of intraocular implants to replace the lens has been in the direction of flexible implants that do not require any enlargement of the incision. An intraocular lens commonly includes a generally disk shaped optic which focuses light on the retina and an outwardly extending haptic portion for proper positioning of the optic within the eye. The flexible nature of the lens enables the lens to be folded and compressed so as to occupy a smaller cross-sectional area for passage through the narrow incision and into the eye. Once inserted through the incision, the lens is permitted to expand to its original size and shape.

A number of devices have been developed to insert a flexible intraocular lens through a small incision in the eye. For example, U.S. Pat. No. 4,681,102 to Bartell uses a hinged cartridge that closes about a lens to fold the lens into a narrower configuration. The cartridge is placed into an inserter mechanism, which advances the folded lens into the eye. The inserter, however, requires several components to be manipulated and assembled during the operation. U.S. Pat. No. 5,275,604 to Rheinish et al. pushes the lens through a narrowing lumen formed with grooves, which act to fold the lens into a smaller size as the lens is pushed toward the eye. The manufacture of spiraling grooves in a tapering lumen is difficult if not impossible to accomplish in a practical manner. In U.S. Pat. No. 5,304,182 to Rheinish et al., a curling member is shifted laterally to fold the lens into a size small enough to pass through the narrow incision. However, no locking arrangement is provided to ensure complete closing of the curling member.

As the lens is released from an inserter into the eye, the resiliency of the lens causes the lens to open and resume its natural shape. However, the considerable folding and/or compression of the lens required in order to pass the lens through the inserter and a small incision, can require considerable force and place a significant amount of pressure on the lens. As a result, the lens is frequently discharged from the inserter with considerable force and velocity. This forceful, uncontrolled release of the lens places the interior of the eye at risk of being injured.

Further, many inserters due to friction do not maintain control of the orientation of the lens as the lens is advanced into the eye. Consequently, the lens may rotate or turn about a longitudinal axis as a result of friction or areas of friction as the lens is pushed through the inserter. Most lenses, however, are made to be set within the eye in a specific orientation. Accordingly, such turning of the lens can result in the lens being placed in the eye in an improper orientation.

SUMMARY OF THE INVENTION

The present invention relates to methods for enhancing the lubricity of implant delivery devices, such as but not limited to intraocular lens inserters. Intraocular lens inserters in accordance with the present invention may be manufactured from a variety of suitable materials, such as for example, but not limited to polycarbonate and polypropylene. To enhance the lubricity of such devices a lubricating agent is typically used. In accordance with the preferred method of the present invention, it has been found that in lubricating polypropylene intraocular lens inserters, the best lubricants are relatively low melting point alpha ($\alpha$) form fatty acid monoglycerides. It has long been recognized that naturally occurring fats and oils (triglycerides) can exist in more than one crystalline form, a phenomenon called polymorphism. Desirable monoglyceride lubricants of the present invention exhibit polymorphism, changing between a least stable $\alpha$ form, a beta prime ($\beta'$) form of intermediate stability and a relatively stable beta ($\beta$) form. The $\alpha$ form is the most desirable form from a lubricative properties perspective. Hence, lubricity may be enhanced by controlling the polymorphism exhibited by the lubricant. Accordingly, the preferred method of the present invention converts one or more relatively high melting point polymorphs to one or more relatively low melting point polymorphs to enhance lubricity and thereby reduce the force required to express an intraocular lens from the delivery device into an eye.

DETAILED DESCRIPTION OF THE INVENTION

Methods of the present invention include a thermal treatment to enhance the lubricity of implant delivery devices, such as but not limited to intraocular lens (IOL) inserters. Lubricity enhancement may be measured by measuring the reduced force required to express an IOL from thermally treated vs. control devices. In addition to lubricity enhancement, thermal treatment in accordance with the present invention also increases the useful shelf-life of the devices. Methods of the present invention are potentially applicable to any delivery device or IOL inserter manufactured from a polymeric composition that relies for lubrication on the "blooming" of an internal lubricant or on coating with an external lubricant. Suitable lubricants for purposes of the present invention include for example but are not limited to one or more saturated fatty acid monoglycerides, i.e., a glyceryl monoester of a saturated fatty acid, such as for example but not limited to glyceryl monolaurate (GML), glyceryl monomyristate (GMM), glyceryl monopalmitate (GMP), glyceryl monostearate (GMS), glyceryl monoarachidate (GMA), glyceryl monobehenate (GMB), glyceryl monolignocerate (GMG), glyceryl monomontanate (GMT) or combinations thereof.

In order for an IOL, such as but not limited to a silicone IOL, to be successfully delivered through a delivery device, such as the MPort™ inserter (Bausch & Lomb Incorporated, Rochester, N.Y.), a lubricant, such as GMS, must first bloom or migrate to the tip surface, or otherwise be present on the surface, such as in the form of a coating. It has been found that delivery performance of inserters decreases over time and with storage at elevated temperatures, even though the amount of lubricant on the tip surface increases under each condition. In studying the same, it was demonstrated that the force required to deliver or express an IOL from an inserter is dependent on the crystalline form of the lubricant found on the surface of the inserter.

A preferred lubricant, such as GMS for example, can exist in at least three major crystalline forms, i.e., α, β' and β. Poor inserter performance has been found to be associated with and perhaps caused by the presence of the most stable crystalline form, i.e., the β polymorph of GMS, and better inserter performance has been found to be associated with the less stable forms, i.e., the α and β' polymorphs of GMS. In studying inserters, poor performing inserters were made to perform better by heating the inserters just above the melting point of the stable β form to regenerate the lower melting point, more lubricious α form upon cooling to room temperature. The presence of different crystal forms of GMS on the surface of the inserters was demonstrated by the differing melting points of the polymorphs as measured by Differential Scanning Calorimetry (DSC).

In accordance with the methods of the present invention, the usable lifetime or shelf-life of inserters can be improved and performance variability can be reduced by heat treatment of the inserters at approximately the melting point of the β form of the fatty acid monoglyceride or above at some point in the manufacturing process, either before or after sterilization of the inserter. In one preferred method of the present invention, the thermal treatment method comprises heating polymeric delivery devices having GMS internal lubricant to approximately 70 to 90° C., but more preferably to approximately 74 to 85° C., and most preferably to approximately 76 to 85° C. for approximately 10 minutes to 4 hours, but more preferably approximately 15 minutes to 2 hours, and most preferably approximately 20 minutes to 1 hour. Generally speaking, as the treatment temperature is increased, the required amount of time decreases, and as the treatment temperature is decreased, the required amount of time increases. Also, while thermal treatment improves inserter lubricity if performed either before or after ethylene oxide (EtO) sterilization, performing thermal treatment after EtO sterilization serves to maximize inserter lubricity. Methods of the present invention for increasing delivery device lubricity are described in still greater detail in the examples provided below.

Example 1

Polymorphism in Glycerol Monostearate/Glycerol Monopalmitate and its Effects on Inserter Lubricity Two hundred and fifteen (215) MPort inserters were obtained from the same lot, i.e., Lot S7860, which was two months old at the time of testing. Of these inserters, forty-three (43) inserters (Group A) were used for initial Instron and DSC characterization. Another forty-three (43) inserters (Group C) were aged at approximately −24° C. for 72 hours and then characterized in the same manner as those of Group A. One hundred and twenty-nine (129) of the 215 inserters were heated at 60° C. for 72 hours. Forty-three (43) of the 129 heated inserters (Group B) were characterized in the same manner as those of Group A and the remaining eighty-six (86) inserters were heated at 85° C. for 20 minutes. Forty-three (43) of the 86 heated inserters (Group D) were characterized in the same manner as those of Group A. The remaining forty-three (43) of the 86 heated inserters (Group E) were heated at 60° C. for 72 hours and characterized in the same manner as those of Group A.

All Instron testing was performed at a crosshead rate of 200 mm/min. Amvisc Plus™ (Bausch & Lomb Incorporated) was used as the external lubricant and saleable SoFlex™ (Bausch & Lomb Incorporated), Model LI61U, +21D, Lots 62CF, 60RD and 62RX, intraocular lenses served as the test lenses. Instron results are summarized below in Table 1.

TABLE 1

Instron Results

| Group | Force, g | SD, g | Number Tested |
|-------|----------|-------|---------------|
| A     | 648      | 129   | 20            |
| B     | 913      | 252   | 20            |
| C     | 578      | 145   | 20            |
| D     | 404      | 36    | 20            |
| E     | 314      | 26    | 20            |

DSC testing on inserter tips was performed with a Model 2920 Modulated DSC (TA Instruments, New Castle, Del.). Each tip (3 tips per condition) was used to fill two pans and both pans were run from −50° C. to 230° C. at 10° C. per minute. Endotherms falling between 0° C. and 100° C. were examined. DSC results are summarized below in Table 2.

TABLE 2

Differential Scanning Calorimetry Results

| Group | Peak Endotherm, ° C. |
|-------|----------------------|
| A     | 78                   |
| B     | 79.5                 |
| C     | 77                   |
| D     | 72.5                 |
| E     | 73                   |

Based on the peak endotherm temperatures observed by DSC, it is apparent that the additive on the surface of Group A and Group B tips is predominately in the β form (77-80° C.) and the additive on the surface of Group D and Group E tips is predominately in the α form (72-73° C.).

The results of this study show that inserter performance is likely related to the crystalline form of GMS. The β polymorph, the higher melting point crystalline form, is not conducive to good lubrication. The lower melting point α polymorph appeared to be a better lubricant.

Example 2

Thermal Treatment of MPort Inserters

A study was performed to identify an effective temperature range for thermal treatment to reduce the delivery force required to expel lenses from MPort inserters. The study found that 70° C. was too low to achieve maximum force reduction and 90° C. was too high. The best results were obtained at 80° C. Heating MPort inserters in the range of 75 to 85° C. was found to improve inserter performance by reducing the force required for lens expression. Heating MPort inserters at temperatures at 60° C. or below or above 100° C. was found to increase the expression force required.

The thermal treatment study involved heating MPort inserters for various periods of time and at various temperatures as summarized below in Table 3.

TABLE 3

Test Sample Matrix

| Inserter Group | Conditioning | No. of Inserters Instron/DSC | No. of Inserters GC |
|---|---|---|---|
| 1 | None, Control | 16 | 5 |
| 2 | 70° C., 10 min. | 16 | 5 |
| 3 | 70° C., 40 min. | 16 | 5 |
| 4 | 70° C., 70 min. | 16 | 5 |
| 5 | 80° C., 10 min. | 16 | 5 |
| 6 | 80° C., 40 min. | 16 | 5 |
| 7 | 80° C., 70 min. | 16 | 5 |
| 8 | 90° C., 10 min | 16 | 5 |
| 9 | 90° C., 40 min. | 16 | 5 |
| 10 | 90° C., 70 min. | 16 | 5 |

Nine groups of inserters were heat-treated over 3 days (one day for each oven set point). The oven was first pre-heated to the desired set point. Thirty-five (35) fully assembled and unboxed inserters were spread out on a wire oven rack at room temperature (RT). The rack was placed in the oven for the desired time plus 1 minute, i.e. 11, 41 and 71 min. After cooling to RT, the inserters were placed in polyethylene (PE) bags and stored at 5° C. until testing was performed.

A summary of the Instron, DSC and gas chromatograph (GC) results is set forth below in Table 4. DSC analyses were performed by physically scraping bloomed additive from the rear loading deck and finger flange areas of the inserters into sample pans. Analyses were run from 0° C. to 100° C. at 5° C. per minute using a DSC7 instrument (Perkin-Elmer, Norwalk, Conn.). Quantitative analysis of the amount of bloomed GMS was done by rinsing the inner lumen of the tips with chloroform and analysis of the extracts by gas chromatography.

TABLE 4

Study Results

| Inserter Group | Instron, F | Instron, SD | DSC | Surface |
|---|---|---|---|---|
| 1 | 642 | 78 | 74.3 | 18 |
| 2 | 421 | 40 | 75.4 | 18 |
| 3 | 452 | 40 | 75.4 | 16 |
| 4 | 459 | 43 | 75.7 | 20 |
| 5 | 319 | 52 | 69.7 | 16 |
| 6 | 322 | 38 | 69.2 | 6 |
| 7 | 321 | 69 | 68.8 | 9 |
| 8 | 361 | 84 | 69.2 | 9 |
| 9 | 524 | 60 | IS | <2 |
| 10 | 1065 | 182 | IS | <2 |

Instron, F = Average Instron Force in grams
Instron, SD = Instron Standard Deviation in grams
DSC = Major DSC Endotherms in degrees Celsius
Surface = Surface concentration of lubricant in micrograms per tip
IS = Insufficient amount of sample for testing The delivery force was most markedly reduced at the three 80° C. intervals. Prolonged heating at 90° C. had a negative effect as compared to the unheated Control lot. Heating at 70° C. gave an intermediate reduction in force compared to the 80° C. and Control groups.

The DSC data indicated that the 70° C. inserters' lubricant did not melt and that the 80° C. inserters' lubricant did melt, forming the α polymorph on cooling. The 10-min., 80° C. inserters' lubricant appears to have only partially melted as evidenced by two melting endotherms. At 90° C., no DSC data could be obtained for the 40- and 70-minute samples because there was insufficient lubricant on the surface to scrape off.

The GC data indicated that the amount of lubricant additive present on the surface after treatment is dependent both on time and temperature. At 70° C., the amount of GMS on the surface remained fairly constant over the three measured intervals. At 80 and 90° C., there was a reduction in the amount of GMS with increased time suggesting that the GMS re-dissolved into the polypropylene.

Example 3

Refinement of Thermal Treatment of Inserters

A further study was performed to identify an effective temperature range for thermal treatment to reduce the delivery force required to expel lenses from inserters. Study results indicate that at 76° C., the inserters can be exposed for as little as 15 minutes and as long as 4 hours to give optimum performance as measured by minimum delivery force. At 80 and 84° C., the exposure range for optimum performance were 15 minutes to 2 hours and 15 minutes to 1 hour, respectively. The degradation in delivery force with prolonged heating is explained by an absence of GMS on the inserter surface.

Heating inserters above the melting point of GMS was found to improve inserter performance, i.e. require less delivery force than non-heated controls. There is a time and temperature range wherein insertion or delivery forces can be reduced through thermal treatment. The lower temperature limit for maximum effectiveness is believed to be the melting point of the β polymorph, i.e., 76° C. The upper temperature limit was found to be 90° C., but the exposure time must be brief, e.g., no more than 10 minutes. At temperatures above the melting point of GMS, the GMS ceases to bloom and most likely re-dissolves into the polypropylene. The rate of dissolution increases with temperature, so surface GMS can be maintained for a much longer time at 80° C. than at 90° C.

A test matrix identifying the number of inserters to be heated under each condition was established and set forth below in Table 5.

TABLE 5

Test Sample Matrix

| Time/Temperature | 76° C. | 80° C. | 84° C. |
|---|---|---|---|
| 15 minutes | 20 - Group 1 | 20 - Group 6 | 20 - Group 11 |
| 30 minutes | 20 - Group 2 | 20 - Group 7 | 20 - Group 12 |
| 1 hour | 20 - Group 3 | 20 - Group 8 | 20 - Group 13 |
| 2 hours | 20 - Group 4 | 20 - Group 9 | 20 - Group 14 |
| 4 hours | 20 - Group 5 | 20 - Group 10 | 20 - Group 15 |

Twenty additional inserters were assigned to Group 16, the "non-treated condition" or control group; thus the total number of test inserters totaled 320.

Thermal treatment was performed on fully assembled, unpackaged inserter units. A calibrated Blue-M forced-air oven was used for conditioning. The oven was pre-heated to the desired set point. Twenty test units were spread out on a wire rack at RT and placed in the oven for 15 minutes. On a second rack, twenty test units were placed in the oven for the designated 30-minute interval. The same procedure was followed for the 1 hour, 2 hour and 4 hour designated intervals.

The clock was started when the oven door was closed. After cooling to RT, each set of inserters was refrigerated at 5° C. until testing was performed.

For each designated interval, the following tests were performed.
1. Instron delivery (10 units per interval) using Amvisc Plus™ (Bausch & Lomb, Incorporated) at 200 mm/min. Peak force was recorded. Five of the 10 units were obtained from DSC analysis (see below). SoFlex™ Model LI61U intraocular lenses (+20 D, +20.5 D, +21 D, +21.5 D and +22 D) served as the test lenses (2 powers each per test).
2. Five (5) units at each interval were reserved for DSC testing. Surface additive was scraped off the rear loading deck and finger flange areas into DSC pans and run from 0 to 100° C. at 5° C./min. Since the amount of GMS that could be scraped from an inserter varied, one to five inserters were used per pan, one pan per interval. After the GMS was scraped from the non-functional areas of the inserter, five units were used for Instron testing (see above).
3. Five (5) units at each interval were reserved for GC testing.

A limited amount of DSC testing was carried out. Analysis of the surface scrapings from Group 1 (the least thermally exposed group) established that the surface additive had melted and recrystallized in the α polymorph (endotherm at 69.7° C.). By comparison, control Group 16 scrapings gave an endotherm at 75.4° C. The remainder of the 76° C.-treated units were tested with similar results to that of Group 1, but there were fewer scrapings with increased exposure time. Since the GMS melted in 15 minutes at 76° C., it was unnecessary to run the remaining samples that had been exposed to higher temperatures for longer periods of time.

A summary of the Instron, DSC and gas chromatograph (GC) results is set forth below in Table 6.

TABLE 6

Study Results

| Sample group | Condition | Instron, F | Instron, SD | DSC | Surface |
|---|---|---|---|---|---|
| 1 | 76° C. - 15 min. | 361 | 12 | 69.7 | 6.0 |
| 2 | 76° C. - 30 min. | 358 | 25 | 69.5 | 4.6 |
| 3 | 76° C. - 1 hour | 356 | 23 | 69.5 | 3.1 |
| 4 | 76° C. - 2 hours | 346 | 32 | 69.2 | 1.9 |
| 5 | 76° C. - 4 hours | 353 | 22 | NR | 1.6 |
| 6 | 80° C. - 15 min. | 331 | 17 | 69.9 | 6.1 |
| 7 | 80° C. - 30 min. | 325 | 16 | NR | 2.7 |
| 8 | 80° C. - 1 hour | 322 | 18 | NR | 1.1 |
| 9 | 80° C. - 2 hours | 335 | 26 | NR | ≦0.4 |
| 10 | 80° C. - 4 hours | 381 | 36 | NR | ≦0.4 |
| 11 | 84° C. - 15 min. | 350 | 23 | NR | 6.8 |
| 12 | 84° C. - 30 min. | 356 | 28 | NR | 2.7 |
| 13 | 84° C. - 1 hour | 352 | 21 | NR | 2.0 |
| 14 | 84° C. - 2 hours | 404 | 36 | NR | ≦0.4 |
| 15 | 84° C. - 4 hours | 645 | 127 | NR | ≦0.4 |
| 16 | Control - not heated | 516 | 62 | 75.4 | 7.1 |

Instron, F = Average Instron Force in grams
Instron, SD = Instron Standard Deviation in grams
DSC = Major DSC Endotherms in degrees Celsius
Surface = Surface concentration of lubricant in micrograms per tip
NR = Not recorded Heat treatment reduced the average delivery force from 516 g to the mid-300 g range. At 76° C., there was no appreciable difference in delivery force between the 15-minute and 4-hour designated intervals. At 80° C., average delivery force increased at the 4-hour interval. At 84° C., delivery force increased at the 2-hour interval and continued to increase at the 4-hour interval. Thus, the maximum exposure times for lowest delivery force were 4 hours, 2 hours and 1 hour at 76, 80 and 84° C. respectively.

The Instron delivery force results can be explained by the amount of GMS (in the α polymorph form) present on the surface of the inserter devices. Surface GMS concentration was observed to decrease with time at all temperatures studied, and the rate of decrease was proportional to temperature. Good deliveries were observed as long as some detectable level of GMS was present and in some cases even when no additive was detected, e.g. 80° C., 2 hours. However, nondetectable levels of GMS were usually associated with higher delivery forces. The detection limit for GMS by GC was about 0.4 μg/tip.

Example 4

Evaluation of 85° C. Heat Treatment Before and After Ethylene Oxide (EtO) Sterilization In the present study, inserters were heat treated at 85° C. before and after EtO sterilization and compared to Control samples to determine which location in the manufacturing process thermal treatment would provide the most benefit. The inserters were aged at 50° C. for 12 weeks to determine the interval over which heat treatment might be effective. It was clearly demonstrated that a post-EtO heat treatment process was preferred. As evaluated by aging at 50° C., pre-EtO heat treatment was only marginally better than no heat treatment. Post-EtO heat-treated inserters performed well even after 12 weeks at 50° C. At each interval, the inserters were characterized by Instron delivery force, by GC for the quantity of surface GMS, and by DSC for the crystalline form of GMS.

Heat treatments were performed on unpackaged, fully assembled MPort inserters by placing wire trays (2×50 to 60 units each) in a pre-heated forced-air oven at 85° C. for 30 minutes. The inserters were air-cooled on the trays overnight. Inserters to be aged were wrapped in aluminum foil (20 per interval) for aging in a forced-air oven maintained at 50° C. Aged samples were stored in a 5° C. walk-in refrigerator until the day of analysis. In most cases, aged inserters were scraped for DSC analysis on the day of removal from aging. Instron data was obtained in most cases within 3 to 4 days after expiration of the aging interval. Instron delivery force was obtained at 200 mm/minute using Amvisc Plus. SoFlex Model LI61U IOLs were used exclusively. The lens power ranges were +20 to +22 D. GC samples were refrigerated for the longest periods prior to analysis. GC analyses of surface rinsed tips were performed as described previously.

The sample inserters were heat treated in accordance with the test sample matrix of Table 7 below. Study results are set forth below in Table 8 below.

TABLE 7

Test Sample Matrix

| Sample | Conditions |
|---|---|
| Group A | As molded, no treatment |
| Group B | EtO sterilization only (Control) |
| Group C | 85° C. heat treatment only |
| Group D | 85° C. heat treatment followed by EtO sterilization |
| Group E | EtO sterilization followed by 85° C. heat treatment |

TABLE 8

Study Results

| Sample | Group | Condition | Instron, F | Instron, SD | DSC | Surface |
|---|---|---|---|---|---|---|
| 1 | A | As molded | 603 | 77 | IS | ≦0.4 |
| 2 | B | As molded + EtO | 313 | 24 | 75.0 | 19.4 |
| 3 | B | 2 wks | 749 | 142 | 75.7 | 114 |
| 4 | B | 4 wks | 702 | 98 | 75.9 | 150 |
| 5 | B | 6 wks | 929 | 249 | 75.2 | 247 |
| 6 | B | 12 wks | 880 | 172 | 74.8 | 202 |
| 7 | C | As molded + 85° C. | 566 | 83 | IS | ≦0.4 |
| 8 | D | 85° C. + EtO | 304 | 35 | 69.5 | 13.7 |
| 9 | D | 2 wks | 452 | 26 | 75.4 | 117 |
| 10 | D | 4 wks | 534 | 60 | 75.0 | 164 |
| 11 | D | 6 wks | 623 | 139 | 74.6 | 209 |
| 12 | D | 12 wks | 746 | 151 | 69.9 | 245 |
| 13 | E | 85° C. + EtO | 368 | 85 | 69.0 | 7 |
| 14 | E | 2 wks | 348 | 35 | 69.7 | 81 |
| 15 | E | 4 wks | 371 | 24 | 75.0 | 88 |
| 16 | E | 6 wks | 381 | 68 | 74.8 | 138 |
| 17 | E | 12 wks | 478 | 73 | 74.1 | 152 |

Instron, F = Average Instron Force in grams
Instron, SD = Instron Standard Deviation in grams
DSC = Major DSC Endotherms in degrees Celsius
Surface = Surface concentration of lubricant in micrograms per tip
IS = Insufficient amount of sample for testing
Wks = weeks Study results show that at the initial interval the forces for Groups B, D and E were nearly equal. With aging, Groups B and D exhibited much higher delivery forces, while Group E did not increase in delivery force so drastically. The bloom rates of GMS for Groups B and D were nearly the same, while the bloom for Group E was somewhat less. In general, higher delivery force was associated with higher additive bloom.

Accordingly, the present study clearly demonstrated that the 85° C. heat treatment was most beneficial when performed after EtO sterilization. The sterilization process had a negative impact on heat treatment. Average inserter delivery force increased with aging. This occurred in all three study groups, but was less prevalent in the post-EtO heat treatment group. The delivery force increase was associated with increasing amounts of GMS on the surface and higher melting point crystalline polymorphs.

Example 5

Shelf-Life Stability of MPort Inserters Using 85° C. Treatment Before Sterilization Thermal treatment or heating MPort inserters to 85° C. was found to enhance inserter performance as described below. Inserter performance was enhanced presumably by melting the undesirable β crystalline form of GMS and forming the more desirable α form. In the present study, the useful lifetime of MPort inserters treated at 85° C. immediately before sterilization was assessed. To promote additive blooming prior to the 85° C. thermal treatment and subsequent sterilization, assembled parts were first heat treated at 50 and 60° C. for 24 hours. Test and control inserters were aged at 25° C. and at 50° C. and characterized at different intervals by Instron, DSC and GC.

A single lot of 640 inserters were assembled. Of the 640 inserters, 200 assembled units were retained for use as controls (Group A). Another 220 assembled inserter units were placed on oven trays and heated in a forced-air oven for 24 hours at 50° C. (Group B). Another 220 assembled inserter units were placed on oven trays and heated in a forced-air oven for 24 hours at 60° C. (Group C). Two hundred units from Group B and two hundred units from Group C were then heat treated at 85° C. for 20 minutes. Units from Groups A, B and C were then packaged and sterilized in accordance with standard operating procedures. The units were then aged at room temperature and at 50° C., the results of which are set forth below in Table 9.

TABLE 9

Study Results

| Sample | Group | Condition | Instron, F | Instron, SD | DSC | Surface |
|---|---|---|---|---|---|---|
| 1 | A | As molded | 859 | 243 | IS | ≦0.4 |
| 2 | A | Post EtO | 410 | 134 | 75.0 | 5.5 |
| 3 | A | 2 wks, 50° C. | 991 | 201 | 75.2 | 81.9 |
| 4 | A | 4 wks, 50° C. | 834 | 138 | 75.2 | 183.2 |
| 5 | A | 6 wks, 50° C. | 1170 | 311 | 75.0 | 103.9 |
| 6 | A | 2 wks, 25° C. | 569 | 182 | 74.6 | 16.8 |
| 7 | A | 4 wks, 25° C. | 481 | 34 | 75.0 | 7.0 |
| 8 | A | 8 wks, 25° C. | 582 | 135 | 74.3 | 19.9 |
| 9 | A | 13 wks, 25° C. | 679 | 94 | 73.9 | 15.5 |
| 10 | A | 26 wks, 25° C. | 596 | 93 | 73.9 | 26.4 |
| 11 | B | Post 50° C. | 354 | 29 | 71.5 | 12 |
| 12 | B | Post 50° C. & 85° C. | 301 | 27 | 68.8 | IS |
| 13 | B | Post EtO | 359 | 138 | 75.0 | 6.3 |
| 14 | B | 2 wks, 50° C. | 790 | 231 | 75.2 | 82.2 |
| 15 | B | 4 wks, 50° C. | 703 | 111 | 75.0 | 186.5 |
| 16 | B | 6 wks, 50° C. | 1125 | 348 | 75.0 | 108.6 |
| 17 | B | 2 wks, 25° C. | 438 | 186 | 74.8 | 6.4 |
| 18 | B | 4 wks, 25° C. | 375 | 34 | 74.8 | 6.6 |
| 19 | B | 8 wks, 25° C. | 419 | 35 | 74.3 | 18.7 |
| 20 | B | 13 wks, 25° C. | 540 | 67 | 74.3 | 20.2 |
| 21 | B | 26 wks, 25° C. | 422 | 60 | 73.9 | 31.6 |
| 22 | C | Post 60° C. | 349 | 21 | 73.7 | 10.0 |
| 23 | C | Post 60° C. & 85° C. | 298 | 13 | 68.8 | 4.0 |
| 24 | C | Post EtO | 321 | 32 | 74.8 | 10.8 |
| 25 | C | 2 wks, 50° C. | 611 | 115 | 75.0 | 73.2 |
| 26 | C | 4 wks, 50° C. | 804 | 189 | 74.8 | 186.2 |
| 27 | C | 6 wks, 50° C. | 974 | 192 | 74.6 | 107 |
| 28 | C | 2 wks, 25° C. | 402 | 122 | 74.3 | 11.2 |
| 29 | C | 4 wks, 25° C. | 383 | 27 | 74.8 | 11.2 |
| 30 | C | 8 wks, 25° C. | 423 | 48 | 74.3 | 18.9 |
| 31 | C | 13 wks, 25° C. | 522 | 57 | 74.3 | 20.9 |
| 32 | C | 26 wks, 25° C. | 433 | 104 | 73.9 | 29.6 |

Instron, F = Average Instron Force in grams
Instron, SD = Instron Standard Deviation in grams
DSC = Major DSC Endotherms in degrees Celsius
Surface = Surface concentration of lubricant in micrograms per tip
IS = Insufficient amount of sample for testing
Wks = weeks For purposes of the present study, room temperature (RT) was defined as ambient room temperature, 25±2° C. Accelerated aging was carried out in a forced-air oven maintained at 50° C. Oven-aged samples were removed from their packaging to conserve oven space. At each interval, the following tests were performed.

1. Instron delivery (10 units per interval) using Amvisc Plus at 200 mm/minute. Peak force was recorded. Five of the 10 units were obtained from DSC analysis (see below). SoFlex Model LI61U IOLs (+20 D, +20.5 D, +21 D, +21.5 D, and +22 D) were used as the test lenses (2 powers each per interval).
2. Five (5) inserter units at each interval were reserved for DSC testing. Surface additive was scraped off the rear loading deck and finger flange areas into DSC pans and run from 0 to 100° C. at 5° C./minute. Since the amount capable of being scraped from an inserter varied, one to five inserters were used per pan, one pan per interval. After additive was scraped from the non-functional areas of the inserter(s), the five units were used for Instron testing (see above).

3. Five (5) units at each interval were reserved for GC testing.

Thermal treatment of inserters at 80° C. and above resulted in a decrease of additive concentration at the surface. It was felt that there may not be sufficient surface additive on as-molded parts to have residual surface additive after the 85° C. treatment. For this reason assembled inserters were heated at 50° C. and 60° C. for 24 hours to effect blooming prior to the 85° C. treatment. As-molded inserters had no detectable surface additive (quantitation limit=0.4 µg/tip). Heating for 24 hours at 50° C. and 60° C. produced additive surface concentrations of 12 and 10 µg/tip respectively. As expected, 85° C. treatment reduced surface additive levels to <0.4 µg/tip and 4 µg/tip, respectively. After EtO sterilization, the additive concentrations for Groups A, B and C were 5.5, 6.3 and 10.8 µg/tip respectively.

Bloomed samples exhibited two DSC endotherms in the 71 to 74° C. range. A lower melting endotherm was indicated for post-85° C. Groups B and C attributed to the α polymorph. Post EtO samples appeared to be β form only (Group A) or mixtures of α and β forms (Groups B and C).

As-molded inserters had a relatively high average delivery force (859 g) and a 40% failure rate. Sterilization decreased the average delivery force to 410 g for Group A inserters. Bloomed samples delivered IOLs with an average force of approximately 350 g. Heat treatment at 85° C. further reduced average delivery force to the 300 g range. Sterilization increased the average delivery force to 359 g and 321 g for Groups B and C respectively.

The average delivery force for inserters aged for 2-, 4- and 6-weeks at 50° C. were measured. At two weeks, there appeared to be a clear advantage for Group C inserters, but this reduced delivery force disappeared at 4- and 6-weeks. All groups increased significantly in force with aging at 50° C. The bloom rates for the 50° C.-aged inserters were also measured. All three groups bloomed heavily and at the same rate.

The average delivery forces for inserters aged for 2-, 4-, 8-, 13- and 26-weeks at 25° C. were measured. Average delivery forces increased less drastically than at 50° C. Group A inserters increased in delivery force by 45% after 26 weeks, while Groups B and C increased by only 18% and 35% respectively. Overall, in terms of average delivery force, Groups B and C delivered lenses at 174 g and 163 g less than Group A samples at 26 weeks. The bloom rates for the 25° C.-aged inserters were also measured. All three groups bloomed additive at similar rates and at a significantly reduced level compared to that of the 50° C.-aged inserters. In conclusion, heat treatment of MPort inserters at 85° C. for 20 minutes before EtO sterilization was an effective means of reducing average Instron inserter force.

Example 6

Shelf-Life Stability of MPort Inserters Using 80° C. Treatment After Sterilization Thermal treatment or heating MPort inserters to 80° C. for 60 minutes after EtO sterilization was found to enhance inserter performance as described below. Inserter performance was enhanced presumably by melting the undesirable β crystalline form of GMS and forming the more desirable a form. In the present study, the useful lifetime of MPort inserters treated at 80° C. immediately after sterilization was assessed. Test and Control inserters were aged at 5° C., 25° C. and 50° C. and characterized at different intervals by Instron, DSC and GC.

A single lot of 560 sterilized MPort inserters was used in the study. Half of the inserters were unpackaged and heat treated at 80° C. for 60 minutes. These Test units were aged in polyethylene bags. The remaining 280 Control units were aged in the original packaging at 5° C. and 25° C., and in polyethylene bags at 50° C. The sample matrix is set forth below in Table 10, and the study results are set forth below in Table 11.

TABLE 10

Test Sample Matrix

| Condition | No. of Test Samples (80° C. Treated) | No. of Control Samples (Non-treated) |
|---|---|---|
| Initial | 20 | 20 |
| 4 Weeks @ 5° C. | 20 | 20 |
| 8 Weeks @ 5° C. | 20 | 20 |
| 13 Weeks @ 5° C. | 20 | 20 |
| 26 Weeks @ 5° C. | 20 | 20 |
| 52 Weeks @ 5° C. | 20 | 20 |
| 2 Weeks @ 25° C. | 20 | 20 |
| 4 Weeks @ 25° C. | 20 | 20 |
| 8 Weeks @ 25° C. | 20 | 20 |
| 13 Weeks @ 25° C. | 20 | 20 |
| 26 Weeks @ 25° C. | 20 | 20 |
| 2 Weeks @ 50° C. | 20 | 20 |
| 4 Weeks @ 50° C. | 20 | 20 |
| 6 Weeks @ 50° C. | 20 | 20 |

TABLE 11

Study Results

| Condition | Sample | Instron, F | Instron, SD | DSC | Surface |
|---|---|---|---|---|---|
| Initial | Test | 320 | 21 | 69.0 | 8.2 |
| | Control | 456 | 16 | 75.0 | 18.9 |
| 5° C., 4 Weeks | Test | 334 | 31 | 68.8 | 8.8 |
| | Control | 475 | 55 | 75.0 | 12.5 |
| 5° C., 8 Weeks | Test | 369 | 23 | 69.2 | 4.3 |
| | Control | 499 | 29 | 75.2 | 12.0 |
| 5° C., 13 Weeks | Test | 322 | 18 | 69.2 | 2.5 |
| | Control | 439 | 31 | 75.2 | 9.8 |
| 5° C., 26 Weeks | Test | 394 | 30 | 69.2 | 4.9 |
| | Control | 502 | 43 | 75.2 | 6.7 |
| 5° C., 52 Weeks | Test | 327 | 20 | 68.8 | 11.7 |
| | Control | 467 | 35 | 75.2 | 26.5 |
| 25° C., 2 Weeks | Test | 332 | 21 | NR | 10.6 |
| | Control | 547 | 30 | NR | 23.7 |
| 25° C., 4 Weeks | Test | 378 | 21 | 67.7 | 10.7 |
| | Control | 543 | 39 | 75.0 | 15.9 |
| 25° C., 8 Weeks | Test | 445 | 16 | 68.1 | 6.1 |
| | Control | 572 | 30 | 75.4 | 18.7 |
| 25° C., 13 Weeks | Test | 382 | 31 | 67.7 | 1.8 |
| | Control | 511 | 57 | 74.6 | 10 |
| 25° C., 26 Weeks | Test | 469 | 35 | 67.3 | 10.3 |
| | Control | 585 | 51 | 74.6 | 12.3 |
| 50° C., 2 Weeks | Test | 383 | 21 | NR | 70.7 |
| | Control | 751 | 91 | NR | 101.9 |
| 50° C., 4 Weeks | Test | 413 | 35 | 69.5 | 74.8 |
| | Control | 684 | 68 | 75.2 | 109.2 |
| 50° C., 6 Weeks | Test | 494 | 61 | 74.6 | 99.5 |
| | Control | 812 | 122 | 75.9 | 134.1 |

Instron, F = Average Instron Force in grams
Instron, SD = Instron Standard Deviation in grams
DSC = Major DSC Endotherms in degrees Celsius
Surface = Surface concentration of lubricant in micrograms per tip
NR = Not recorded For purposes of the present study, room temperature (RT) was defined as ambient room temperature, 25±2° C. Accelerated aging was carried out in a forced-air oven maintained at 50±2° C. Refrigerated aging was carried out at 5±2° C. At each interval, the following tests were performed.

1. Instron delivery (10 units per interval) using Amvisc Plus at 200 mm/minute. Peak force was recorded. Five of the 10 units were obtained from DSC analysis (see below). SoFlex Model LI61U IOLs (+20 D, +20.5 D, +21 D, +21.5 D, and +22 D) were used as the test lenses (2 powers each per interval).
2. Five (5) inserter units at each interval were reserved for DSC testing. Surface additive was scraped off the rear loading deck and finger flange areas into DSC pans and run from 0 to 100° C. at 5° C./minute. Since the amount capable of being scraped from an inserter varies, one to five inserters were used per pan, one pan per interval. After additive was scraped from the non-functional areas of the inserter(s), the five units were used for Instron testing (see above).
3. Five (5) units at each interval were reserved for GC testing.

Instron delivery force data for 50° C.-aged inserters is set forth in Table 11. The Test groups of inserters increased in average delivery force from 320 g to 494 g after 6 weeks at 50° C. The Control group increased from 456 g to 812 g over the same time frame. The Control group had a higher bloom than the Test group at each interval. Both groups bloomed heavily compared to 25- and 5-° C.-aged inserters. No DSC data was taken at the 2-week interval. At the 4- and 6-week intervals, the Test group samples showed evidence for mixed α and β polymorphs with more β polymorph at 6 weeks and more α polymorph at 4 weeks. The Control group samples indicate β polymorph only at 4 weeks (75° C.) and predominately β polymorph at 6 weeks.

Instron delivery force data for 25° C.-aged inserters is set forth in Table 11. The Test groups of inserters increased in average delivery force from 320 g to 469 g after 26 weeks at 25° C. The Control group increased from 456 g to 585 g over the same time frame. The Control group had a higher bloom than the Test group at each interval. The amount of additive on the surface for each group appeared to decrease with time. Because this trend is contrary to previous test results and prevailing logic, the observed effect is attributed to limitations of the test method. By comparing these results with the 50° C. data above, it is seen that 6 weeks at 50° C. is not equivalent to 26 weeks at 25° C. as predicted by the Arrhenius expression (acceleration factor=1.8", where n=(50−25)/10.

No DSC data was taken at the 2-week interval.

Instron delivery force data for 5° C.-aged inserters is set forth in Table 11. The Test and Control inserters did not increase in average delivery force over the 52-week period at 5° C. The Control group had a higher bloom than the Test group at each interval. The amount of additive on the surface for each group was variable. The DSC thermograms of the Test group samples were straightforward at 5° C. and clearly indicated the presence of the α polymorph out to 52 weeks. The endotherms of the Control samples were likewise straightforward, with the β polymorph endotherm predominating at every interval.

It was shown in the present study that 80° C. heat treatment after sterilization was effective in reducing average inserter force relative to untreated controls at every interval and temperature studied. The reason for the force reduction appears consistent with the presence of the α polymorph of GMS.

While there is shown and described herein a process for improving IOL inserter lubricity and thereby improved IOL delivery, it will be manifest to those skilled in the art that various modifications may be made without departing from the spirit and scope of the underlying inventive concept and that the same is not limited to particular processes and structures herein shown and described except insofar as indicated by the scope of the appended claims.

We claim:

1. An intraocular lens inserter tip with enhanced lubricity comprising predominately one or more lower melting point polymorphs of one or more lubricants at a surface of the intraocular lens inserter tip, wherein material scraped from the surface of the intraocular lens inserter tip exhibits a DSC endotherm of from 68.8 to 73, and the lower melting point polymorphs form by melting corresponding higher melting point polymorphs of the one or more lubricants.

2. The intraocular inserter tip of claim 1 wherein said lubricants are selected from the group consisting of glyceryl monolaurate, glyceryl monomyristate, glyceryl monopalmitate, glyceryl monostearate, glyceryl monoarachidate, glyceryl monobehenate, glyceryl monolignocerate, glyceryl monomontanate and combinations thereof.

3. The intraocular inserter tip of claim 1 wherein said one or more lower melting point polymorphs are selected from the group consisting of alpha polymorphs of monoglycerides.

4. The intraocular inserter tip of claim 1 wherein said one or more lower melting point polymorphs is the alpha polymorph of glyceryl monostearate.

5. The intraocular inserter tip of claim 1 wherein said device contains polypropylene.

6. The intraocular inserter tip of claim 1 wherein said one or more lower melting point polymorphs reduce the force required to express an intraocular lens into an eye.

7. An intraocular lens inserter tip with enhanced lubricity comprising:
polypropylene and one or more lower melting point, alpha polymorphs of one or more monoglycerides present in the polypropylene, wherein the concentration of the one or more lower melting point polymorphs is predominantly greater than the corresponding higher melting point polymorphs of the one or more monoglycerides which are selected from the group consisting of glyceryl monolaurate, glyceryl monomyristate, glyceryl monopalmitate, glyceryl monostearate, glyceryl monoarachidate, glyceryl monobehenate, glyceryl monolignocerate and glyceryl monomontanate, and material scraped from a surface of the polypropylene inserter tip exhibits a DSC endotherm of from 68.8 to 73.

8. The intraocular inserter tip of claim 7 wherein said one or more lower melting point polymorphs is the alpha polymorph of glyceryl monostearate.

9. An intraocular inserter prepared by a process comprising:
providing an intraocular inserter tip comprising a polymer selected from polypropylene or polycarbonate, and one or more lubricants; and
heat treating the intraocular inserter at a temperature from 60° C. to 90° C. for a time sufficient to convert a predominant amount of the beta-polymorph to the corresponding alpha-polymorph of the one or more lubricants, and to provide a surface material of the polypropylene inserter tip, which when physically scrapped from the tip exhibits a DSC endotherm of from 68.8 to 73.

10. The intraocular inserter of claim 9 wherein the one or more lubricants are glyceryl monoesters of a saturated fatty acid.

11. The intraocular inserter of claim 9 wherein the one or more lubricants are selected from the group consisting of glyceryl monolaurate, glyceryl monomyristate, glyceryl monopalmitate, glyceryl monostearate, glyceryl monoarachidate, glyceryl monobehenate, glyceryl monolignocerate and glyceryl monomontanate.

12. The intraocular inserter of claim 9 wherein the one or more lubricants includes glyceryl monostearate.

13. The intraocular inserter of claim 12 wherein the heat treating is conducted at a temperature from 70° C. to 85° C. for a period of from fifteen minutes to four hours.

14. The intraocular inserter of claim 13 wherein sterilizing the intraocular inserter is conducted prior to the heat treating.

15. The intraocular inserter of claim 9 further comprising sterilizing the intraocular inserter by contacting the inserter with ethylene oxide.

16. The intraocular inserter of claim 15 wherein sterilizing the intraocular inserter is conducted prior to the heat treating.

17. The intraocular inserter of claim 15 wherein sterilizing the intraocular inserter is conducted after the heat treating.

18. The intraocular inserter of claim 9 wherein the heat treating is conducted at a temperature from 70° C. to 85° C. for a period of from fifteen minutes to four hours.

19. An intraocular inserter prepared by a process comprising:

providing an intraocular inserter tip comprising polypropylene and one or more glyceryl monoesters of a saturated fatty acid;

contacting the intraocular inserter with ethylene oxide; and heat treating the intraocular inserter at a temperature from 60° C. to 90° C. for a time sufficient to convert a predominant amount of the beta-polymorph to the corresponding alpha-polymorph of the one or more glyceryl monoesters of a saturated fatty acid, and to provide a surface material of the polypropylene inserter tip, which when physically scrapped from the tip exhibits a DSC endotherm of from 68.8 to 73.

20. The intraocular inserter of claim 19 wherein the heat treating is conducted at a temperature from 70° C. to 85° C. for a period of from fifteen minutes to four hours.

21. The intraocular inserter of claim 20 wherein the one or more lubricants are selected from the group consisting of glyceryl monolaurate, glyceryl monomyristate, glyceryl monopalmitate, glyceryl monostearate, glyceryl monoarachidate, glyceryl monobehenate, glyceryl monolignocerate and glyceryl monomontanate.

22. The intraocular inserter of claim 20 wherein the one or more lubricants includes glyceryl monostearate.

* * * * *